United States Patent [19]

Pryor et al.

[11] 4,327,232

[45] Apr. 27, 1982

[54] CYCLOPROPANE RING-CONTAINING COMPOUNDS AS INHIBITOR COMPONENTS IN METHYLCHLOROFORM

[75] Inventors: Alvetta Pryor, Houston; Nobuyuki Ishibe, Lake Jackson, both of Tex.

[73] Assignee: The Dow Chemical Company, Midland, Mich.

[21] Appl. No.: 235,883

[22] Filed: Feb. 19, 1981

[51] Int. Cl.$^3$ .............................................. C07C 17/42
[52] U.S. Cl. .................... 570/108; 570/110; 570/115; 570/116; 570/118; 570/121
[58] Field of Search ............... 570/108, 110, 115, 116, 570/118, 121

[56] References Cited

U.S. PATENT DOCUMENTS

| | | | |
|---|---|---|---|
| 2,190,512 | 10/1959 | Ferri et al. | 570/121 X |
| 3,049,571 | 8/1962 | Brown | 570/108 X |
| 3,201,482 | 8/1965 | Fredenburg | 570/108 |
| 3,864,413 | 2/1975 | Beckers et al. | 570/121 X |
| 3,974,230 | 8/1976 | Archer et al. | 570/110 X |

FOREIGN PATENT DOCUMENTS

| | | | |
|---|---|---|---|
| 755667 | 3/1971 | Belgium | 570/121 |
| 52-3004 | 1/1977 | Japan | 570/110 |

*Primary Examiner*—Thomas A. Waltz
*Attorney, Agent, or Firm*—A. C. Ancona

[57] ABSTRACT

A stabilized methylchloroform solvent useful in degreasing operations in which the alkylene oxide stabilizer component normally employed is replaced by a tricyclic or quadricyclic compound containing a fused cyclopropane ring.

6 Claims, No Drawings

CYCLOPROPANE RING-CONTAINING COMPOUNDS AS INHIBITOR COMPONENTS IN METHYLCHLOROFORM

BACKGROUND OF THE DISCLOSURE

Methylchloroform is particularly susceptible to decomposition in the presence of metals, especially when aluminum and iron are present. Stabilizers are known which are effective in stabilizing methylchloroform against decomposition induced by contact with iron and aluminum even at elevated temperatures, such as are encountered in vapor degreasing and processes involving purification by distillation.

It is also known, however, that while pure uninhibited methylchloroform at elevated temperatures is relatively inert to the presence of zinc, methylchloroform which is stabilized against decomposition due to contact with other metals, particularly iron and aluminum, tends to decompose badly in the presence of zinc and cause substantial corrosive attack on the zinc metal. Decomposition of the solvent and corrosion of the zinc occur only when the zinc is exposed to the hot vapors of methylchloroform stabilized against iron and aluminum induced decomposition. Zinc below the surface of the boiling solvent will remain virtually unaffected. This is due to the fact that these inhibitors, which stabilize methylchloroform against iron and aluminum, catalyze the attack of methylchloroform on zinc in the boiling vapors of the solvent. This undesirable property causes a restriction of the utility of methylchloroform particularly as a solvent in the vapor degreasing field as galvanized equipment is common and many of the articles to be degreased are zinc or zinc alloy, such as brass or galvanized iron.

An additional need for a stabilizer system to render the hot vapors of methylchloroform inert to zinc surfaces is found in the recovery of used solvent. Methylchloroform may be used in the cold degreasing of metals until it becomes saturated with dirt, grease and other impurities from the metal being cleaned. Spent solvent without the stabilizer system hereinafter proposed cannot be recovered by distillation in the zinc-lined stills commonly used in the industry without damage to the lining thereof.

Methylchloroform where used as a vapor degreasing solvent contains minor amounts of certain additives or stabilizers to prevent decomposition of the solvent induced by its contact with metals such as aluminum and iron. Inhibitors such as 1,4-dioxane alone or in combination with nitromethane, secondary butyl alcohol, or monohydric acetylenic alcohols are commonly employed. Such stabilizers are quite effective in rendering the solvent inert to attack of the metal by the degradation products, but greatly increase the ability of zinc, in the boiling solvent vapors, to cause degradation of the solvent and concomitantly increased attack of the metal. This undesirable property of the solvent may be eliminated, however, by the addition thereto of a vicinal monoepoxide in the amount of from about 0.01 to 5.0 percent by weight of the solvent mixture.

Numerous formulations which contain the epoxide are known to the literature. Thus, for example in U.S. Pat. No. 3,099,694 an epoxide, together with dioxolane and a monoolefin, is employed as stabilizer for methylchloroform. In U.S. Pat. No. 3,265,747 methylchloroform is stabilized with the combination of a lower dialkyl ketone and an epoxide. More recently U.S. Pat. No. 3,974,230 employs methyl butynol, t-amyl alcohol, a nitroalkane and an epoxide in a formulation for stabilizing methylchloroform used in degreasing operations.

It has now been found unexpectedly that the epoxide can be substituted with an alicyclic compound which contains a cyclopropane ring, particularly those tricyclic and quadricyclic compounds having a fused cyclopropane ring in their structure.

A cyclopropane ring compound in which the ring is not fused into a larger cyclic structure is disclosed in our copending application Ser. No. 212,649, filed Dec. 3, 1980. In that disclosure the compound employed is cyclopropyl methyl carbinol.

SUMMARY OF THE INVENTION

Alicyclic compounds which contain a cyclopropane ring fused into a larger cyclic structure have been found useful as a substitute for the epoxide in formulations of stabilizers employed to protect methylchloroform in the presence of metals. Such formulations have been found effective in vapor degreasing applications, especially when metals such as aluminum, zinc, copper, and iron are present. Concentration of the alicyclic compound preferably is at approximately the same level as that of the alkylene oxide it replaces. Thus, the preferred amount is from about 0.5 to about 1 volume percent in the stabilized methylchloroform solvent, but as little as 0.2% and as much as 2% is operable in the composition of the invention.

DETAILED DESCRIPTION OF THE INVENTION

As representative of formulations useful in stabilizing methylchloroform employed in degreasing operations is one in U.S. Pat. No. 3,974,230. Experiments were performed which show that the cyclopropane ring compounds can be effectively substituted for the epoxide in that formulation.

Formulations according to U.S. Pat. No. 3,974,230 may contain by volume from 1.75 to 3.5% 2-methyl-3-butyn-2-ol, 0 to 4.25% of t-amyl alcohol, 0.5 to 2% nitroalkane and 0.5 to 1% of an alkylene oxide. The nitroalkane may be nitromethane or a mixture thereof with nitroethane.

EXAMPLE 1

A formulation in accordance with the above mentioned patent was tested by refluxing the stabilized material and its top and bottom distilled fractions, i.e. fractions of the composition which would correspond to that found in the vapor section and sump section, respectively, of a vapor degreaser. The formulations containing the epoxide and the same formulations in which the cyclopropane ring compounds had been substituted for the epoxide were tested against certain metals. Approximately 430 g of each formulation was partitioned by distillation into 1:1 fractions. Ten milliliter aliquots of both fractions and the non-fractionated solution were refluxed for seven days in the presence of Al-2024, Zn, Cu, brass, steel, and iron and the solvent stability was rated. A formulation according to the '230 patent containing the epoxide was tested as above and compared with the same formulation in which the epoxide had been replaced with one of the cyclopropane ring-containing compounds. The formulation according to the '230 patent contained 2.0 vol. % 2-methyl-3-butyn-2-ol, 2.0 vol. % t-amyl alcohol, 0.4 vol. % nitromethane, 0.5 vol. % butylene oxide or the test compound. The results are shown in Table I.

TABLE I

| Formulations* | 2024 Aluminum Coupon | 2024 Aluminum Chips | Zinc Coupon | Zinc Mossy | Ratings** Mossy Zn + Al Chips | Copper | Brass | Steel Wool | Iron Filings |
|---|---|---|---|---|---|---|---|---|---|
| A. Butylene oxide (Comparative) | | | | | | | | | |
| a | 0 | 0 | 0 | 0 | 0 | 1 | 1 | 1 | 0 |
| b | 0 | 0 | 0 | 0 | 0 | 1 | 2 | 1 | 0 |
| c | 0 | 0 | 0 | 0 | 0 | 1 | 1 | 0 | 0 |
| B. Nortricyclyl formate*** | | | | | | | | | |
| a | 0 | 0 | 0 | 0 | 0 | — | 0 | — | — |
| C. Quadricyclane | | | | | | | | | |
| a | 0 | 0 | 0 | 0 | 0 | 0 | 1 | 2 | 1 |
| b | 0 | 0 | 0 | 0 | 0 | 1 | 0 | 0 | 0 |
| c | 0 | 0 | 0 | 0 | 1 | 0 | 0 | 1 | 0 |

*a unfractionated solution
b top fraction
c bottom fraction
**The ratings are on a scale of 0–5, zero being substantially no corrosion and clear solvent, while 5 indicates heavy corrosion and discolored, decomposed solvent.
***Contained 0.6% volume nitroethane (in addition to the nitromethane)

EXAMPLE 2

In another test in which the same formulation was prepared, but containing norcarane and norbornylene each in place of the butylene oxide in separate formulations, the unfractionated stabilizer was tested by refluxing in the presence of zinc coupons and mossy zinc for seven days. The results are shown in Table II.

TABLE II

| Epoxide Substitute | Zn Coupons 0.5% | Zn Coupons 1.0% | Mossy Zn 0.5% | Mossy Zn 1.0% |
|---|---|---|---|---|
| Norcarane | 0 | 0 | 1 | 2 |
| Norbornylene (comparative) | 0 | 0 | 0 | 5 |

We claim:

1. In a stabilizer formulation useful in stabilizing methylchloroform used in vapor degreasing wherein said formulation contains an alkylene oxide as a component of said stabilizer, the improvement which comprises employing a bicyclic, a tricyclic or a quadricyclic compound which contains a fused cyclopropane ring in place of the epoxide in said formulation.

2. A stabilizer formulation according to claim 1 which contains from 1.75 to 3.5% 2-methyl-2-butyn-2-ol, 0 to 4.25% of t-amyl alcohol, 0.5 to 2% nitroalkane and 0.2 to 2% of said tricyclic or quadricyclic compound based on the total volume of methylchloroform and stabilizers.

3. The composition of claim 2 wherein the tricyclic or quadricyclic compound is present in a concentration of from about 0.5 to about 1.0%.

4. The composition of claim 2 wherein the tricyclic compound is nortricyclyl formate.

5. The composition of claim 2 wherein the quadricyclic compound is quadricyclane.

6. The composition of claim 2 wherein the bicyclic compound is norcarane.

* * * * *

UNITED STATES PATENT AND TRADEMARK OFFICE
CERTIFICATE OF CORRECTION

PATENT NO. : 4,327,232
DATED : April 27, 1982
INVENTOR(S) : Alvetta Pryor and Nobuyuki Ishibe It is certified that error appears in the above—identified patent and that said Letters Patent is hereby corrected as shown below:

On the title page

Under the References Cited, first patent listed, change "2,190,512" to --2,910,512--.

Signed and Sealed this

Thirty-first Day of August 1982

[SEAL]

Attest:

GERALD J. MOSSINGHOFF

Attesting Officer     Commissioner of Patents and Trademarks